(12) United States Patent
Hamada et al.

(10) Patent No.: US 7,321,055 B2
(45) Date of Patent: Jan. 22, 2008

(54) PRODUCTION METHOD OF OPTICALLY ACTIVE DEPHENYLALANINE COMPOUNDS

(75) Inventors: Takayuki Hamada, Kawasaki (JP); Masayuki Oshita, Kawasaki (JP); Masanobu Yatagai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/498,752

(22) Filed: Aug. 4, 2006

(65) Prior Publication Data

US 2007/0032658 A1 Feb. 8, 2007

(30) Foreign Application Priority Data

Aug. 4, 2005 (JP) .............................. 2005-227077

(51) Int. Cl.
*C07C 229/00* (2006.01)
(52) U.S. Cl. ...................... 562/441; 562/401; 562/402; 546/136
(58) Field of Classification Search ................ 562/441, 562/401, 402; 546/136
See application file for complete search history.

(56) References Cited

U.S. PATENT DOCUMENTS

| | | | |
|---|---|---|---|
| 5,198,548 A * | 3/1993 | Beylin et al. ................ | 546/136 |
| 6,632,816 B1 | 10/2003 | Stranix et al. | |
| 2004/0167341 A1 | 8/2004 | Haffner et al. | |
| 2004/0180928 A1* | 9/2004 | Gutman et al. ............. | 514/317 |
| 2004/0242636 A1 | 12/2004 | Haffner et al. | |

FOREIGN PATENT DOCUMENTS

| WO | 03/002531 | 1/2003 |
|---|---|---|
| WO | 2004/056764 | 7/2004 |

OTHER PUBLICATIONS

Chang et al, "An Efficient Synthesis of N-BOC-D-Diphenylalanine From A Chiral Azirdine-2-Carboxylate", *Heterocycles*, 2002, vol. 57, No. 6, pp. 1143-1148.
Chen et al, "Chiral Synthesis of D- and L-3,3-Diphenylalanine (DIP), Unusual α-Amino Acids For Peptides of Biological Interest", *Tetrahedron Letters*, 1992, vol. 33, No. 23, pp. 3293-3296.
H. Chen et al, "Chiral Synthesis of D- and L-3,3-Diphenylalanine (DIP), Unusual α-Amino Acids For Peptides of Biological Interest", *Tetrahedron Letters*, 1992, vol. 33, No. 23, pp. 3293-3296.

* cited by examiner

*Primary Examiner*—Yvonne Eyler
*Assistant Examiner*—Sudhakar Katakam
(74) *Attorney, Agent, or Firm*—Oblon, Spivak, McClelland, Maier & Neustadt, P.C.

(57) ABSTRACT

Optically active diphenylalanine compounds may be conveniently prepared in a good yield by reacting a diphenylalanine compound represented by formula (1) with an optically active amine compound represented by formula (2) in the presence of an organic solvent to give a diastereomeric salt represented by formula (5) and then treating the diastereomeric salt under acidic conditions to give an optically active diphenylalanine compound represented by formula (3):

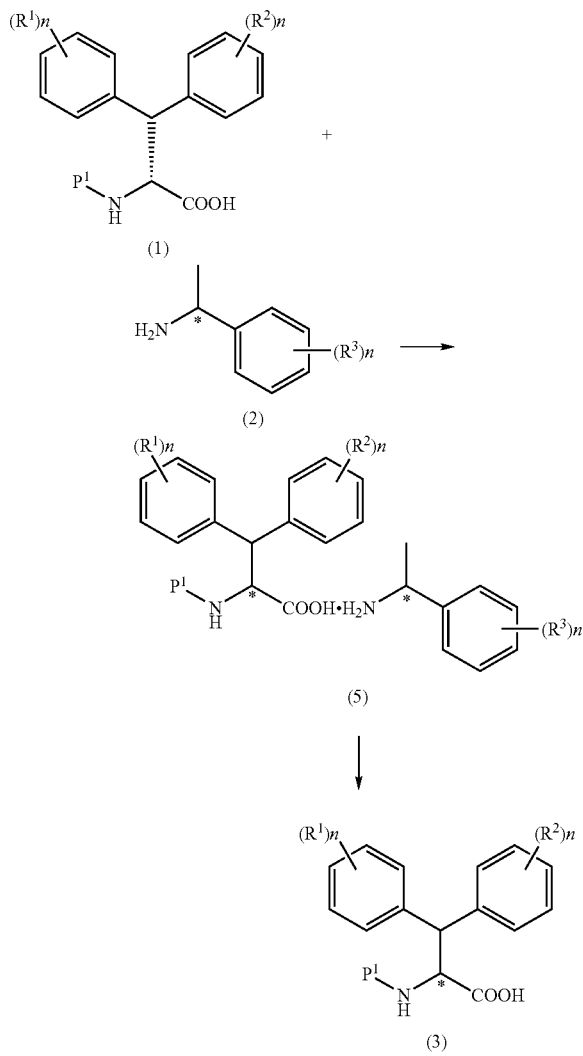

wherein each symbol is as defined in the specification.

26 Claims, No Drawings

PRODUCTION METHOD OF OPTICALLY ACTIVE DEPHENYLALANINE COMPOUNDS

CROSS REFERENCES TO RELATED APPLICATIONS

This application claims priority to Japanese Patent Application No. 2005-227077, filed on Aug. 4, 2005, which is incorporated herein by reference in its entirety.

BACKGROUND OF THE INVENTION

1. Field of the Invention

The present invention relates to methods of producing optically active diphenylalanine compounds, which are useful as synthetic intermediates for anti-HIV drugs, dipeptidyl peptidase inhibitors, and the like. The present invention also relates to diastereomeric salts of the compounds, which are useful for the production of the compounds.

2. Discussion of the Background

Optically active diphenylalanine compounds (including amino group-protected compounds thereof) are useful as synthetic intermediates for pharmaceutical compounds and, for example, used as synthetic intermediates for anti-HIV drugs (see, e.g., WO04/056764 and U.S. Pat. No. 6,632,816) and dipeptidyl peptidase inhibitors (see, e.g., WO03/002531 and U.S. Patent Publication Nos. 2004/0167341 and 2004/0242636).

As the production method of optically active 3,3-diphenylalanine, a method shown in the following reaction scheme is described, which includes reacting N-(diphenylmethylene)glycine ester (synthesized from benzophenoneimine and glycine ester) and diphenylbromomethane to synthesize a racemate of 3,3-diphenylalanine, forming a diastereomeric salt of the racemate with cinchonidine and performing an optical resolution (see, U.S. Pat. No. 5,198,548). As a result of experimental reproduction of the optical resolution method by the present inventors and the like, however, it was found that the optical purity of the obtained D-3,3-diphenylalanine was 86% e.e.

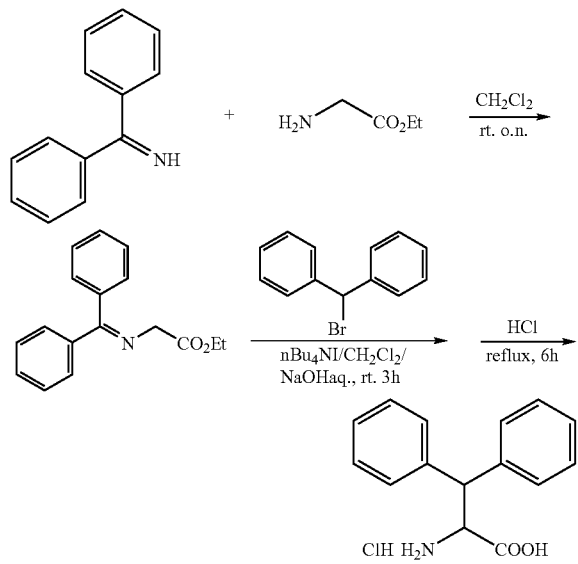

As a different method, *HETEROCYCLES*, vol. 57, no. 6, pp. 1143-1148 (2002) and *Tetrahedron Letters*, vol. 33, no. 23, pp. 3293-3296 (1992) describe asymmetric synthesis methods of N-Boc-diphenylmethylalanine. However, these methods involve the use of a stoichiometric amount of an asymmetric source, and require many steps, a low temperature reaction vessel for the reaction at −78° C. and expensive reagents such as KHMDS and the like, thus leading to high costs. Hence, these methods are hardly industrially advantageous.

Thus, there remains a need for an efficient and low-cost method for producing optically active diphenylalanine compounds. There also remains a need for intermediates which are useful for the production of optically active diphenylalanine compounds.

SUMMARY OF THE INVENTION

Accordingly, it is one object of the present invention to provide novel methods of producing optically active diphenylalanine compounds, which are useful as synthetic intermediates for anti-HIV drugs, dipeptidyl peptidase inhibitors, and the like.

It is another object of the present invention to provide novel methods which are capable of producing an optically active diphenylalanine compound industrially advantageously in a high yield.

It is another object of the present invention to provide novel intermediates which are useful in such methods.

These and other objects, which will become apparent during the following detailed description, have been achieved by the inventors' discovery that optical resolution of an optically active N-protected diphenylalanine compound can be efficiently performed by forming a diastereomeric salt of a N-protected diphenylalanine compound with a particular optically active phenylethylamine compound.

Accordingly, the present invention provides the following:

(1) A method of producing an optically active diphenylalanine compound represented by formula (3):

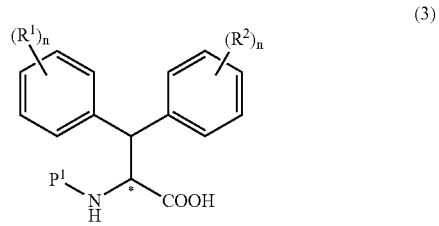

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, each n is independently an integer of 1 to 5, $P^1$ is an amino-protecting group, *indicates an asymmetric carbon atom, and the configuration of each asymmetric carbon atom is S or R, which method comprises:

(i) reacting a diphenylalanine compound represented by formula (1):

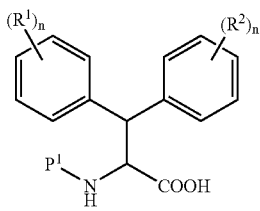

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, each n is independently an integer of 1 to 5, and $P^1$ is an amino-protecting group, with an optically active amine compound represented by formula (2):

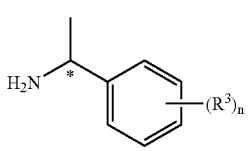

wherein $R^3$ is a hydrogen atom, a halogen atom, a substituted or unsubstituted alkyl group, a substituted or unsubstituted alkoxy group, a hydroxyl group, a protected hydroxyl group, a cyano group, a nitro group, or an acyl group, or two adjacent $R^3$ are optionally condensed to form a benzene ring, n is an integer of 1-5, *indicates an asymmetric carbon atom, and the configuration of each asymmetric carbon is S or R; and (ii) separating the resulting diastereomeric salt:

(2) The method of the above-mentioned (1) wherein the optically active amine compound is one or more kinds selected from the group consisting of respective optically active forms of 1-phenylethylamine, 1-(4-methylphenyl)ethylamine, 1-(4-ethylphenyl)ethylamine, 1-(4-propylphenyl)ethylamine, 1-(4-isopropylphenyl)ethylamine, 1-(4-methoxyphenyl)ethylamine, 1-(4-bromophenyl)ethylamine, 1-(4-chlorophenyl)ethylamine, 1-(4-fluorophenyl)ethylamine, 1-(4-hydroxyphenyl)ethylamine, 1-(4-cyanophenyl)ethylamine, 1-(4-nitrophenyl)ethylamine, 1-(4-acetylphenyl)ethylamine, 1-(1-naphthyl)ethylamine, and 1-(2-naphthyl)ethylamine.

(3) The method of the above-mentioned (1) wherein the optically active amine compound is one or more kinds selected from the group consisting of (−)-1-phenylethylamine, (+)-1-phenylethylamine, (−)-1-(4-methylphenyl)ethylamine, (+)-1-(4-methylphenyl)ethylamine, (−)-1-(4-isopropylphenyl)ethylamine, (+)-1-(4-isopropylphenyl)ethylamine, (−)-1-(4-methoxyphenyl)ethylamine, (+)-1-(4-methoxyphenyl)ethylamine, (−)-1-(4-bromophenyl)ethylamine, (+)-1-(4-bromophenyl)ethylamine, (−)-1-(4-chlorophenyl)ethylamine, (+)-1-(4-chlorophenyl)ethylamine, (−)-1-(1-naphthyl)ethylamine, (+)-1-(1-naphthyl)ethylamine, (−)-1-(2-naphthyl)ethylamine, and (+)-1-(2-naphthyl)ethylamine.

(4) The method of the above-mentioned (1) wherein the optically active amine compound is one or more kinds selected from the group consisting of (−)-1-phenylethylamine, (+)-1-phenylethylamine, (−)-1-(4-methylphenyl)ethylamine, and (+)-1-(4-methylphenyl)ethylamine.

(5) The method of any one of the above-mentioned (1) to (4), wherein the separating comprises crystal precipitation of a diastereomeric salt in one or more kinds of solvents selected from the group consisting of water, methanol, ethanol, 2-propanol, ethyl acetate, benzene, toluene, xylene, cyclohexane, methylcyclohexane, 1,2-dichloroethane, tert-butyl methyl ether, isobutyl methyl ketone, butyl acetate, chlorobenzene, tetrahydrofuran, N,N-dimethylformamide, N,N-dimethylacetamide, dimethyl sulfoxide, N-methyl-2-pyrrolidone, and acetonitrile.

(6) A method of producing an optically active diphenylalanine compound represented by formula (4):

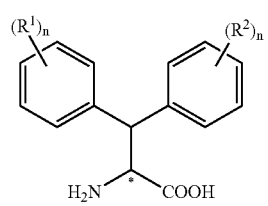

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, a protected hydroxyl group, each n is independently an integer of 1 to 5, *indicates an asymmetric carbon atom, and the configuration of each asymmetric carbon is S or R, or a salt thereof, which method comprises:

(i) obtaining an optically active diphenylalanine compound represented by formula (3) according to the method of any one of the above-mentioned (1) to (5); and (ii) removing the amino-protecting group of the compound.

(7) The method of any one of the above-mentioned (1) to (6), wherein $R^1$ and $R^2$ are each independently a fluorine atom or a hydrogen atom, and $P^1$ is an acetyl group.

(8) A diastereomeric salt represented by formula (5):

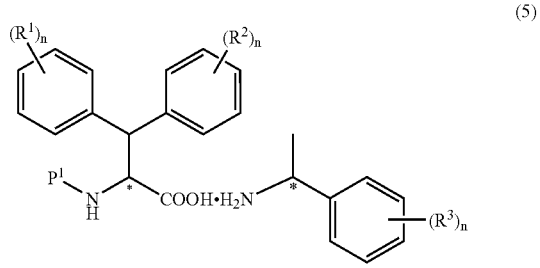

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, $R^3$ is a hydrogen atom, a halogen atom, a substituted or unsubstituted alkyl group, a substituted or unsubstituted alkoxy group, a hydroxyl group, a protected hydroxyl group, a cyano group, a nitro group, or an acyl group, or two adjacent $R^3$ are optionally condensed to form a benzene ring, each n is independently an integer of 1 to 5, $P^1$ is an amino-protecting group, each *indicates an asymmetric carbon atom, and the configuration of each asymmetric carbon atom is S or R.

(9) An optically active N-acetyldiphenylalanine compound (R)-(+)-1-(4-methylphenyl)ethylamine salt represented by formula (6a):

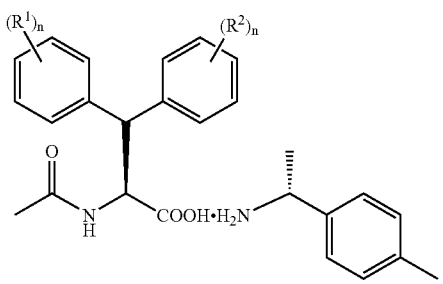

(6a)

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, and each n is independently an integer of 1 to 5.

(10) An optically active N-acetyldiphenylalanine compound (S)-(-)-1-(4-methylphenyl)ethylamine salt represented by formula (6b):

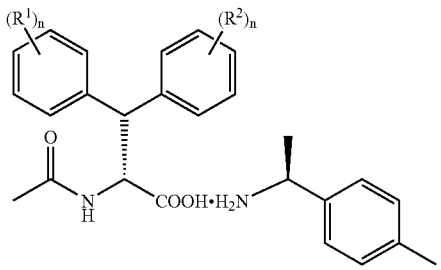

(6b)

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, and each n is independently an integer of 1 to 5.

(11) The salt of the above-mentioned (9) or (10), wherein $R^1$ and $R^2$ are each independently a fluorine atom or a hydrogen atom.

According to the present invention, an optically active diphenylalanine compound having a high purity can be produced conveniently in a high yield.

DETAILED DESCRIPTION OF THE PREFERRED EMBODIMENTS

The present invention is explained in detail in the following. Firstly, the symbols in the formulas in the present specification are defined as follows.

As the halogen atom for $R^1$, $R^2$, or $R^3$, a chlorine atom, a bromine atom, and a fluorine atom are preferable, and a fluorine atom is particularly preferable.

The alkyl group for $R^1$, $R^2$, or $R^3$ refers to a linear or branched alkyl group preferably having 1 to 10, more preferably 1 to 7, still more preferably 1 to 4 carbon atoms. To be specific, a methyl group, an ethyl group, a propyl group, an isopropyl group, a butyl group, an isobutyl group, a sec-butyl group, a tert-butyl group, a pentyl group, a hexyl group, a heptyl group, an octyl group, and the like can be mentioned. Of these, a methyl group, an ethyl group, a propyl group, an isopropyl group, a butyl group, a tert-butyl group, and the like are preferable. The alkyl group is optionally substituted by one or more substituents selected from a halogen atom (e.g., chlorine atom, bromine atom, fluorine atom), a hydroxyl group, an alkoxy group having 1 to 6 carbon atoms (e.g., methoxy group), and the like. In the present invention, the alkyl group encompasses substituted alkyl groups.

As the alkoxy group for $R^1$, $R^2$, or $R^3$, an alkoxy group wherein the alkyl moiety is the aforementioned alkyl group is preferable. To be specific, a methoxy group, an ethoxy group, a propoxy group, an isopropoxy group, a butoxy group, and a tert-butoxy group can be mentioned. Of these, a methoxy group and an ethoxy group are more preferable. The alkoxy group is optionally substituted by one or more substituents selected from a halogen atom (e.g., chlorine atom, bromine atom, fluorine atom), a hydroxyl group, an alkoxy group having 1 to 6 carbon atoms (e.g., methoxy group) and the like. In the present invention, the alkoxy group encompasses substituted alkoxy groups.

The amino group for $R^1$ or $R^2$ is optionally mono- or di-substituted by the aforementioned alkyl group, aryl group or aralkyl group, or optionally substituted by the amino-protecting group for the below-mentioned $P^1$. In the present invention, the amino group encompasses substituted amino groups. As the aryl group, an aryl group having 6 to 14 (preferably 6 to 8) carbon atoms such as a phenyl group, a tolyl group, and the like can be mentioned. As the aralkyl group, a benzyl group and the like can be mentioned.

The hydroxyl group for $R^1$, $R^2$, or $R^3$ is similarly optionally substituted by a protecting group exemplified as the amino-protecting group for the below-mentioned $P^1$. In the present invention, the hydroxyl group encompasses protected hydroxyl groups.

As the amino-protecting group for $P^1$, the substituents described in *Protecting Groups in Organic Chemistry* 2nd edition (John Wiley&Sons, Inc. 1991) can be mentioned. To be specific, an acyl group, an alkyl group, an aralkyl group, a silyl group, and the like can be mentioned. As the acyl group, for example, an acyl group having 1 to 8 carbon atoms such as a formyl group, an acetyl group, a phenylacetyl group, and the like can be mentioned. As the alkyl group and aralkyl group, for example, the aforementioned alkyl group and aralkyl group can be mentioned. As the silyl group, for example, a tri-substituted silyl group such as a trimethylsilyl group, a triethylsilyl group, a tert-butyldimethylsilyl group, and the like can be mentioned. In addition, a methoxymethyl group, a methylthiomethyl group, a benzyloxymethyl group, a methoxyethoxymethyl group, a tetrahydropyranyl group, a methoxycarbonyl group (Moc group), a 9-fluorenylmethoxycarbonyl group (Fmoc group), a 2,2,2-trichloroethoxycarbonyl group, a benzyloxycarbonyl group (Cbz group), a tert-butoxycarbonyl group (Boc group), and the like can be mentioned.

As the acyl group for $R^3$, those similar to the acyl groups exemplified as the amino-protecting group for $P^1$ can be mentioned.

Particularly preferable embodiments for each symbol are as follows.

As $R^1$ and $R^2$, a hydrogen atom, a halogen atom, and an alkyl group having 1 to 10 carbon atoms are preferable, a hydrogen atom and a halogen atom are more preferable, and a hydrogen atom and a fluorine atom are particularly preferable. $R^1$ and $R^2$ may be the same or different.

As $P^1$, an acyl group having 1 to 8 carbon atoms, a Moc group, a Fmoc group, a Cbz group, and a Boc group are preferable, and an acetyl group is particularly preferable.

As $R^3$, a hydrogen atom, a methyl group, an ethyl group, a propyl group, an isopropyl group, a methoxy group, a bromine atom, a chlorine atom, a fluorine atom, a hydroxy group, a cyano group, a nitro group, and an acetyl group are preferable, or two adjacent $R^3$ are preferably condensed to form a benzene ring. $R^3$ is more preferably a hydrogen atom, a methyl group, an isopropyl group, a methoxy group, a bromine atom, or a chlorine atom, or two adjacent $R^3$ are condensed to form a benzene ring, and $R^3$ is particularly preferably a hydrogen atom or a methyl group.

The compound represented by formula (4) may be an acid addition salt thereof and, for example, a salt such as an inorganic acid salt (e.g., hydrochloride, sulfate), an organic acid salt (e.g., acetate, trifluoroacetate, tosylate, mesylate), and the like may be formed.

The production method of the present invention is explained in the following.

The diphenylalanine compound represented by formula (1) needs to be subjected to optical resolution, and is typically obtained as a racemic diphenylalanine compound. It is also possible to use an optically active diphenylalanine compound having a low optical purity and increase its optical purity by the present method. As the optically active diphenylalanine compound having a low optical purity, for example, a mixture of an (R) form and an (S) form, which has an optical purity of not more than 80% e.e. ("e.e." refers to enantiomeric excess), can be mentioned.

In the present invention, an optically active diphenylalanine compound represented by formula (3) (hereinafter to be referred to as compound (3)) is obtained by reacting a diphenylalanine compound represented by formula (1) (hereinafter to be referred to as compound (1)) with an optically active amine compound represented by formula (2) (hereinafter to be referred to as compound (2)), separating the resulting diastereomeric salt represented by formula (5) (hereinafter to be referred to as diastereomeric salt (5)) and converting the salt to compound (3).

The reaction is generally carried out in an organic solvent. As the organic solvent, any solvent can be used as long as it does not inhibit the reaction, and an alcohol organic solvent is preferably used. As the alcohol organic solvent, methanol, ethanol, 1-propanol, 2-propanol, and t-butanol can be mentioned, with particular preference given to methanol. These organic solvents can be used alone or in combination of two or more kinds thereof. Moreover, water or a non-alcohol organic solvent may be added to these alcohol organic solvents. As the non-alcohol organic solvent, ethyl acetate, isopropyl acetate, toluene, xylene, cyclohexane, methylcyclohexane, 1,2-dichloroethane, tert-butyl methyl ether, isobutyl methyl ketone, butyl acetate, chlorobenzene, tetrahydrofuran, N,N-dimethylformamide, N,N-dimethylacetamide, dimethyl sulfoxide, N-methyl-2-pyrrolidone, N-ethyl-2-pyrrolidone, acetonitrile, and the like can be mentioned. The amount of the organic solvent to be used can be appropriately determined depending on the kind of the compound, and is generally 1- to 20-fold weight, preferably 3- to 10-fold weight, based on the weight of compound (1).

The amount of compound (2) to be used is generally 0.5 to 1.5 equivalents, preferably 0.5 to 1.0 equivalent, based on compound (1). The reaction temperature is 40° C. to 70° C., preferably 50° C. to 60° C. The reaction time is 0.1 to 2 hours, preferably 0.5 to 1 hour.

The resulting diastereomeric salt (5) can be separated by crystal precipitation of diastereomeric salt (5) in a solvent.

As the solvent to be used for the separation of the diastereomeric salt (5), those similar to the above-mentioned reaction solvents can be mentioned. Of such solvents, one or more kinds of solvents selected from the group of water, methanol, ethanol, 2-propanol, ethyl acetate, benzene, toluene, xylene, cyclohexane, methylcyclohexane, 1,2-dichloroethane, tert-butyl methyl ether, isobutyl methyl ketone, butyl acetate, chlorobenzene, tetrahydrofuran, N,N-dimethylformamide, N,N-dimethylacetamide, dimethyl sulfoxide, N-methyl-2-pyrrolidone, and acetonitrile are preferable. Methanol is particularly preferable.

The crystal precipitation can be performed, for example, under the following conditions. After completion of the reaction, the reaction mixture is slowly cooled. The time of cooling is 1 to 10 hours, preferably 2 to 5 hours. The temperature after cooling is 0° C. to 30° C., preferably 20° C. to 30° C. Thereafter, the mixture is stirred at said temperature to perform crystal precipitation. The stirring time is 0.5 to 24 hours, preferably 1 to 5 hours. Filtration of the precipitated crystal gives diastereomeric salt (5). Where necessary, a seed crystal may be used.

After obtaining a crystal of diastereomeric salt (5), the salt is converted to compound (3), and the compound (3) is isolated. The conversion and isolation can be performed, for example, by extracting diastereomeric salt (5) with an aprotic organic solvent under acidic conditions.

While the conversion and isolation can be performed by a conventionally known method, for example, a method comprising adding an acid (e.g., hydrochloric acid, sulfuric acid, etc.) to diastereomeric salt (5) in a mixed solvent of an aprotic organic solvent (e.g., ethyl acetate, isopropyl acetate, toluene, etc.) and water can be mentioned. After acidification (generally pH 0.5 to 3, preferably 1 to 2), the mixture is extracted. The obtained organic layer is washed with water, and concentrated or added with a nonpolar organic solvent to give compound (3).

While the amino-protecting group of compound (3) can be removed by a known method, for example, methods such as acid treatment, catalytic reduction and the like can be mentioned. For acid treatment, for example, an acid (e.g., hydrochloric acid, sulfuric acid) is added to compound (3) and the mixture is reacted at generally 80° C. to 100° C. (preferably 90° C. to 100° C.) generally for 1 to 16 hours (preferably 3 to 6 hours). In this case, compound (4) can be obtained as an acid addition salt. When, for example, 2- to 20-fold weight (preferably 5- to 7-fold weight) of concentrated hydrochloric acid is used as the acid, the hydrochloride of compound (4) is precipitated. The precipitate is filtered and dried to give the hydrochloride of compound (4). For catalytic reduction, for example, hydrogen is introduced into compound (4) in the presence of a reduction catalyst such as palladium carbon and the like by a conventionally known method.

According to the present invention, compound (4) having an optical purity of not less than 90% e.e., preferably not less than 95% e.e., more preferably not less than 98% e.e., can be obtained.

As preferable compound (2) in the present invention, one or more kinds selected from the group consisting of respective optically active forms of 1-phenylethylamine, 1-(4-methylphenyl)ethylamine, 1-(4-ethylphenyl)ethylamine, 1-(4-propylphenyl)ethylamine, 1-(4-isopropylphenyl)ethylamine, 1-(4-methoxyphenyl)ethylamine, 1-(4-bromophenyl)ethylamine, 1-(4-chlorophenyl)ethylamine, 1-(4-fluorophenyl)ethylamine, 1-(4-hydroxyphenyl)ethylamine, 1-(4-cyanophenyl)ethylamine, 1-(4-nitrophenyl)ethylamine, 1-(4-acetylphenyl)ethylamine, 1-(1-naphthyl)ethylamine, and 1-(2-naphthyl)ethylamine can be mentioned.

As more preferable compound (2), one or more kinds selected from the group consisting of (−)-1-phenylethylamine, (+)-1-phenylethylamine, (−)-1-(4-methylphenyl)ethylamine, (+)-1-(4-methylphenyl)ethylamine, (−)-1-(4-isopropylphenyl)ethylamine, (+)-1-(4-isopropylphenyl)ethylamine, (−)-1-(4-methoxyphenyl)ethylamine, (+)-1-(4-methoxyphenyl)ethylamine, (−)-1-(4-bromophenyl)ethylamine, (+)-1-(4-bromophenyl)ethylamine, (−)-1-(4-chlorophenyl)ethylamine, (+)-1-(4-chlorophenyl)ethylamine, (−)-1-(1-naphthyl)ethylamine, (+)-1-(1-naphthyl)ethylamine, (−)-1-(2-naphthyl)ethylamine, and (+)-1-(2-naphthyl)ethylamine can be mentioned.

As particularly preferable compound (2), one or more kinds selected from the group consisting of (−)-1-phenylethylamine, (+)-1-phenylethylamine, (−)-1-(4-methylphenyl)ethylamine, and (+)-1-(4-methylphenyl)ethylamine can be mentioned.

The diastereomeric salt of the present invention obtained by the production method of the present invention, which is represented by formula (5):

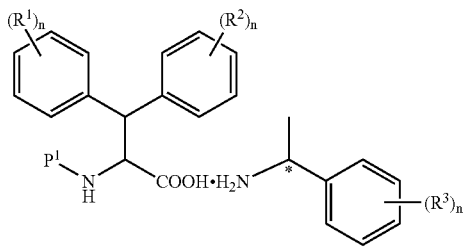

(5)

wherein each symbol is as defined above, is a novel compound.

As particularly preferable diastereomeric salts (5), an optically active N-acetyldiphenylalanine compound (R)-(+)-1-(4-methylphenyl)ethylamine salt represented by formula (6a):

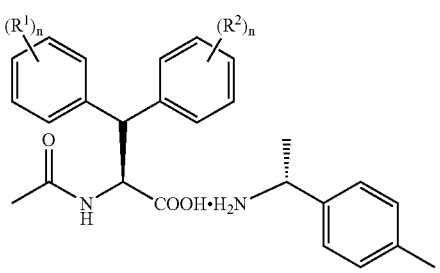

(6a)

wherein each symbol is as defined above, and an optically active N-acetyldiphenylalanine compound (S)-(−)-1-(4-methylphenyl)ethylamine salt represented by formula (6b):

(6b)

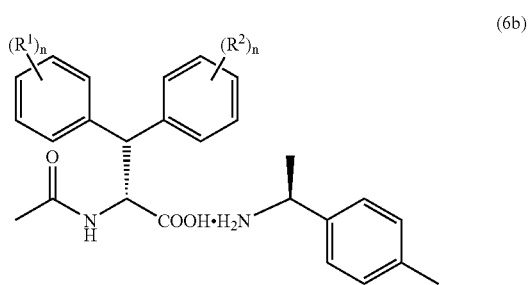

wherein each symbol is as defined above, can be mentioned. These are also novel compounds.

The diphenylalanine compound represented by formula (1) in the present invention can be produced according to the known methods described in U.S. Pat. No. 5,198,548; *HETEROCYCLES*, vol. 57, no. 6, pp. 1143-1148 (2002); or *Tetrahedron Letter*, vol. 33, no. 23, pp. 3293-3296 (1992). More preferably, the compound can be produced by the method shown in the following scheme.

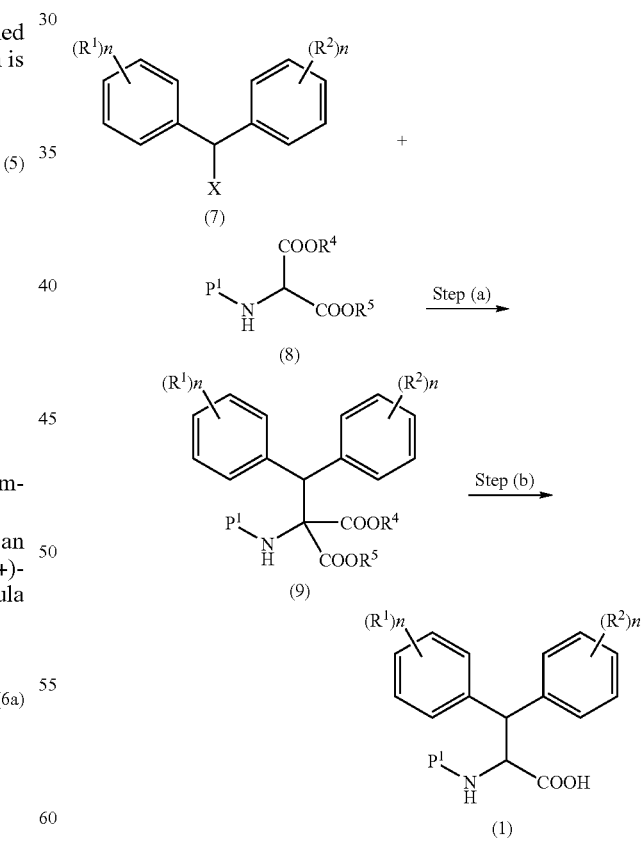

wherein X is a halogen atom, $R^4$ and $R^5$ are each independently an alkyl group or an aralkyl group, or $R^4$ and $R^5$ in combination form an alkylene group, and other symbols are as defined above.

As the halogen atom for X, a chlorine atom, a bromine atom, and an iodine atom are preferable, and a chlorine atom and a bromine atom are particularly preferable.

As the alkyl group for $R^4$ or $R^5$, those similar to the alkyl group for $R^1$, $R^2$, or $R^3$ can be mentioned.

The aralkyl group for $R^4$ or $R^5$ is an alkyl group substituted by an aryl group. The alkyl group preferably has 1 to 6, more preferably 1 to 3, carbon atoms. To be specific, a methyl group, an ethyl group, a propyl group, an isopropyl group, and the like can be mentioned. The aryl group preferably has 6 to 14 (preferably 6 to 8) carbon atoms. To be specific, a phenyl group, a naphthyl group, and the like can be mentioned. The total carbon number of the aralkyl group is preferably 7 to 20, more preferably 7 to 11. To be specific, a benzyl group, a 1-phenylethyl group, a 2-phenylethyl group, and the like can be mentioned. Of these, a benzyl group is preferable. The aralkyl group is optionally substituted by one or more substituents selected from a halogen atom (e.g., fluorine atom), an alkyl group having 1 to 6 carbon atoms (e.g., methyl group), an alkoxy group having 1 to 6 carbon atoms (e.g., methoxy group), a haloalkyl group (e.g., trifluoromethyl group), a haloalkoxy group (e.g., trifluoromethoxy group), and the like.

As the alkylene group formed by $R^4$ and $R^5$ in combination, a linear or branched alkylene group having 2 to 6, more preferably 2 to 4, carbon atoms can be mentioned. To be specific, an ethylene group, a trimethylene group, a propylene group, and a tetramethylene group can be mentioned. Of these, a trimethylene group and a tetramethylene group are preferable.

Step (a)

In Step (a), a diphenylmethylene halide compound represented by formula (7) (hereinafter to be referred to as compound (7)) is reacted with a malonic acid diester compound represented by formula (8) (hereinafter to be referred to as compound (8)) in the presence of an organic solvent selected from N-methyl-2-pyrrolidone, N-ethyl-2-pyrrolidone, and N,N-dimethylformamide, and a base selected from alkali metal hydride and alkali metal t-butoxide to give a diester compound represented by formula (9) (hereinafter to be referred to as compound (9)).

The reaction of Step (a) is carried out in the presence of a base selected from alkali metal hydride and alkali metal t-butoxide. As the alkali metal hydride, for example, lithium hydride, potassium hydride, sodium hydride, and the like can be mentioned, and sodium hydride and potassium hydride are particularly preferable. As the alkali metal t-butoxide, sodium t-butoxide, potassium t-butoxide, and the like can be mentioned, and potassium t-butoxide is particularly preferable. The amount of the above-mentioned base to be used is generally 1 to 1.5 equivalents, preferably 1.1 to 1.3 equivalents, based on compound (8).

To promote the above-mentioned reaction, an iodine compound or a bromine compound may be co-present. In this case, when X is a chlorine atom, the reaction is carried out in the co-presence of an iodine compound and/or a bromine compound, and the reaction is preferably carried out in the presence of an iodine compound. When X is a bromine atom, the reaction is carried out in the presence of an iodine compound.

As the iodine compound, a metal iodide or a quaternary ammonium iodide are preferably used. As the metal iodide, alkali metal iodide is preferable and, for example, lithium iodide, potassium iodide, and sodium iodide can be mentioned. Of these, potassium iodide and sodium iodide are particularly preferable. As the quaternary ammonium iodide, for example, tetrabutylammonium iodide and tetraheptylammonium iodide can be mentioned, and tetrabutylammonium iodide is particularly preferable. As the bromine compound, a metal bromide or a quaternary ammonium bromide are preferably used. As the metal bromide, alkali metal bromide is preferable and, for example, lithium bromide, potassium bromide, and sodium bromide can be mentioned. Potassium bromide and sodium bromide are particularly preferable. As the quaternary ammonium bromide, for example, tetrabutylammonium bromide and tetraheptylammonium bromide can be mentioned, and tetrabutylammonium bromide is particularly preferable. The amount of the iodine compound or bromine compound to be used is generally 0.05 to 1.0 equivalent, preferably 0.5 to 1.0 equivalent, based on compound (7).

The reaction of Step (a) is carried out in an organic solvent selected from N-methyl-2-pyrrolidone (aka N-methylpyrrolidihone or 1-methylpyrrolidinone), N-ethyl-2-pyrrolidone, and N,N-dimethylformamide. For increasing the yield, N-methyl-2-pyrrolidone and N-ethyl-2-pyrrolidone are preferable, and N-methyl-2-pyrrolidone is particularly preferable. N-Methyl-2-pyrrolidone, N-ethyl-2-pyrrolidone, and N,N-dimethylformamide may be used in a mixture of two or more kinds thereof. As long as the effect of the reaction is realized, a solvent other than N-methyl-2-pyrrolidone, N-ethyl-2-pyrrolidone, and N,N-dimethylformamide may be admixed. As such solvent, an aprotic organic solvent is preferably used and, for example, dimethyl sulfoxide, hexamethylphosphoric triamide, acetonitrile, toluene, and the like can be mentioned. The amount of the organic solvent to be used can be appropriately determined depending on the kind of the compound. It is generally 3- to 20-fold weight, preferably 5 to 10-fold weight, based on the weight of compound (7).

The amount of compound (8) to be used is generally 1 to 1.5 equivalents, preferably 1.1 to 1.3 equivalents, based on compound (7). When the amount of compound (8) to be used is less than the above-mentioned range, the reaction tends to be insufficient.

As the reaction conditions when the base is an alkali metal hydride, the reaction temperature is generally 30° C. to 60° C., preferably 40° C. to 50° C., and the reaction time is generally 1 to 16 hours, preferably 3 to 6 hours. When the base is an alkali metal t-butoxide, the reaction temperature is generally 30° C. to 80° C., preferably 60° C. to 70° C., and the reaction time is generally 3 to 24 hours, preferably 3 to 8 hours. After completion of the reaction, an organic solvent (e.g., hydrocarbons such as toluene and the like) and water are added to the reaction mixture to allow partitioning, and the obtained organic layer is washed with water and the like and concentrated to give compound (9). Alternatively, after completion of the reaction, Step (b) may be performed in the same reaction container without working up.

Step (b)

In Step (b), compound (9) is subjected to hydrolysis and decarboxylation to give compound (1). As a result, compound (1) can be obtained conveniently in a high yield.

The hydrolysis and decarboxylation can be performed by a conventionally known method. For example, a method comprising reacting compound (9) with a base (e.g., sodium hydroxide) in an alcohol organic solvent (e.g., ethanol) or a mixed solvent of an alcohol organic solvent and water can be mentioned. The above-mentioned reaction is generally carried out at a temperature within the range of from 80° C. to the refluxing temperature of the solvent used (preferably 85° C. to 90° C.) generally for 1 to 16 hours, preferably 3 to 6 hours. After completion of the reaction, an organic solvent (e.g., hydrocarbons such as toluene and the like) and water are added to the reaction mixture to allow partitioning, acetates (e.g., isopropyl acetate) and water are added to the obtained aqueous layer, an acid (e.g., hydrochloric acid, sulfuric acid) is added to acidify (generally pH 0.5 to 3, preferably 1 to 2), the solution and the solution is extracted. The obtained organic layer is washed with water and the like and concentrated to give compound (1).

Step (a) and Step (b) can also be carried out sequentially in the same reaction container. For example, a method comprising adding, after completion of the reaction of Step (a), a base (e.g., sodium hydroxide, potassium hydroxide, an aqueous solution thereof, etc.) to allow reacting can be mentioned. This reaction is generally carried out at a temperature within the range of from 50° C. to the refluxing temperature of the solvent used (preferably 60° C. to 70° C.) generally for 1 to 16 hours, preferably 3 to 6 hours.

After completion of the reaction, the mixture is partitioned, the obtained aqueous layer is neutralized (generally pH 6 to 8, preferably 7 to 8) with an acid (e.g., hydrochloric acid, sulfuric acid), an acetate (e.g., ethyl acetate, isopropyl acetate) is added thereto, and the mixture is acidified (generally pH 0.5 to 3, preferably 1 to 2) with an acid (e.g., hydrochloric acid, sulfuric acid), and extracted. The obtained organic layer is washed with acid (e.g., hydrochloric acid) and saturated brine and concentrated to give compound (1).

The compound (1) obtained by concentration is amorphous. It is also possible to obtain compound (1) as a crystal by carrying out concentration to an incomplete extent and then cooling the acetate solution, or by crystal precipitation by the addition of a particular poor solvent (e.g., toluene) to the acetate solution.

As noted above, the optically active compounds of formula (3) prepared by the present process are, in turn, useful for preparing anti-HIV drugs and dipeptidyl peptidase inhibitors. Such methods for preparing anti-HIV drugs and dipeptidyl peptidase inhibitors are disclosed in, e.g., WO04/056764, U.S. Pat. No. 6,632,816cWO03/002531, and U.S. Patent Publication Nos. 2004/0167341 and 2004/0242636, all of which are incorporated herein by reference in their entireties.

Thus, the present invention also provides a method for preparing a compound of formula I:

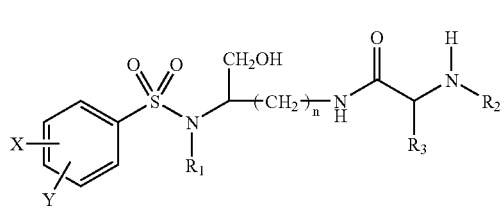

and when the compound of formula I comprises an amino group, pharmaceutically acceptable ammonium salts thereof, wherein n is 3 or 4, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$; —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein $R_1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein $R_2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4—$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

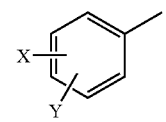

a picolyl group selected from the group consisting of

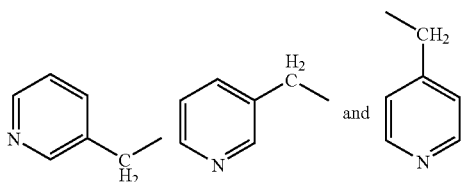

a picolyloxy group selected from the group consisting of

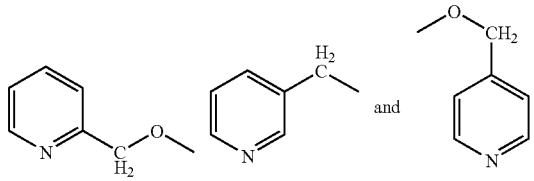

a substituted pyridyl group selected from the group consisting of

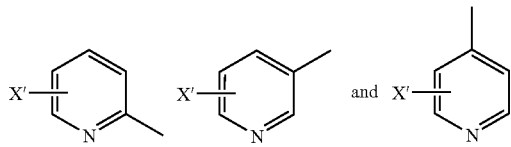

a group selected from the group consisting of

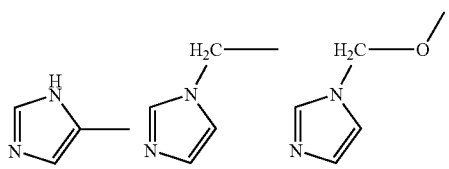

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, and wherein R$_3$ is a diphenylmethyl group of formula IV

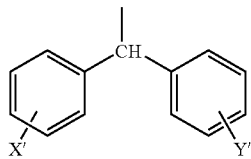

in which a compound of formula (3) is converted into the compound of formula I, and in which the compound of formula (3) is prepared by the present method.

The present invention further provides a method for making a compound of formula II:

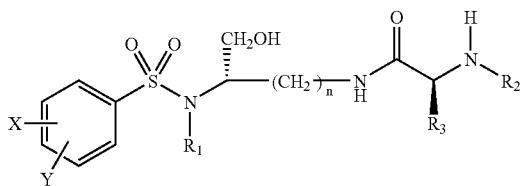

and when the compound of formula II comprises an amino group, pharmaceutically acceptable ammonium salts thereof, wherein n is 3 or 4, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —OR$_4$, —SR$_4$, —COOR$_4$, —COR$_4$, and —CH$_2$OH or X and Y together together define an alkylenedioxy group selected from the group consisting of a methylenedioxy group of formula —OCH$_2$O— and an ethylenedioxy group of formula —OCH$_2$CH$_2$O—, wherein R$_1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R$_2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula R$_{2A}$—CO—, R$_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —CH$_2$OH, —CF$_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

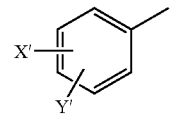

a picolyl group selected from the group consisting of

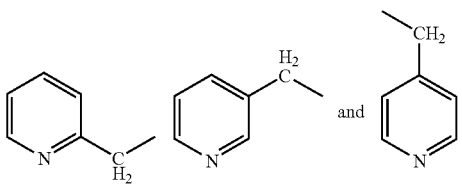

a picolyloxy group selected from the group consisting of

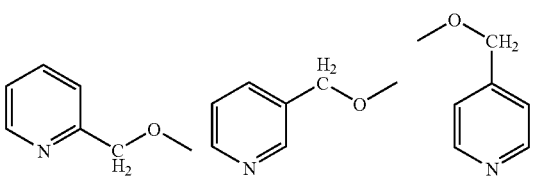

a substituted pyridyl group selected from the group consisting of

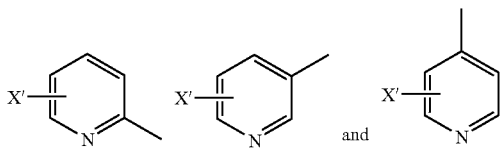
and a group selected from the group consisting of

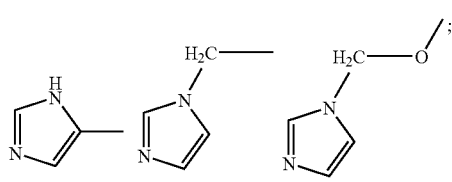
;

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein R$_3$ is a diphenylmethyl group of formula IV

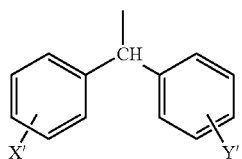

by converting a compound of formula (3) according to the present invention into the compound of formula II, and in which the compound of formula (3) is prepared by the present method.

The present invention further provides a method for making a compound of formula IIa:

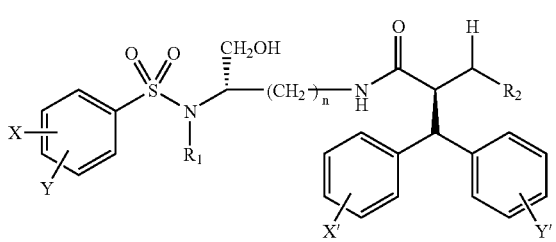

and when the compound of formula IIa comprises an amino group, pharmaceutically acceptable ammonium salts thereof, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —OR$_4$, —SR$_4$, —COOR$_4$, —COR$_4$, and —CH$_2$OH or X and Y together define an alkylenedioxy group selected from the group consisting of a methylenedioxy group of formula —OCH$_2$O— and an ethylenedioxy group of formula —OCH$_2$CH$_2$O—, wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, and wherein n, R$_1$, R$_2$, R$_4$, and R$_5$ are as defined in the compound of formula I, by converting a compound of formula (3) according to the present invention into the compound of formula Ia, and in which the compound of formula (3) is prepared by the present method.

Other features of the invention will become apparent in the course of the following descriptions of exemplary embodiments which are given for illustration of the invention and are not intended to be limiting thereof.

EXAMPLES

Reference Example 1

Synthesis of 2-acetylamino-3,3-diphenylpropanoic acid

To a solution (1.25 M) of diethyl acetamidomalonate (13.33 g, 61.8 mmol) in N-methyl-2-pyrrolidone (40 mL) was added potassium t-butoxide (7.20 g, 64.3 mmol), and the mixture was stirred at room temperature for 1 hour. Diphenylmethylene chloride (10.0 g, 49.3 mmol) and potassium iodide (4.10 g, 24.7 mol) were added, and the mixture was stirred at 70° C. for 6 hours. After completion of the reaction, 2M aqueous sodium hydroxide solution (45 mL) was added to the reaction mixture, and the mixture was stirred for 5 hours at 60° C. After cooling to room temperature, the mixture was partitioned. The aqueous layer was adjusted to pH 7.0 with concentrated hydrochloric acid (4.4 mL), ethyl acetate (30 mL) and then concentrated hydrochloric acid (6.9 mL) were added, and the aqueous layer was extracted. The aqueous layer was further extracted with ethyl acetate (40 mL). The organic layers were combined, washed 3 times with 2M hydrochloric acid (20 mL), washed with saturated brine (10 mL), and concentrated. Toluene (30 mL) was added to the concentrate, and the mixture was concentrated at 50° C. Toluene (30 mL) was further added, and the mixture was stirred for 30 minutes. The mixture was cooled to 0° C. over 5 hours to allow precipitation of white crystals. The crystals were collected by filtration and dried under reduced pressure to give the title compound (11.69 g). The powder X-ray (Cu—Kα ray) of the dry crystals showed characteristic peaks at 5.8°, 11.5°, 21.6°, 23.2°, and 28.7°.

Reference Example 2

Synthesis of 2-acetylamino-3,3-bis(4-fluorophenyl)propanoic acid

To a solution (1.25M) of diethyl acetamidomalonate (5.17 g, 23.80 mmol) in N-methyl-2-pyrrolidone (18.2 mL) was added potassium t-butoxide (2.77 g, 24.69 mmol), and the mixture was stirred for 1 hour at room temperature. A solution (21.79 g) of bis(4-fluorophenyl)methylene chloride (4.54 g, 19.02 mmol) in toluene and potassium iodide (3.19 g, 19.10 mol) were added, and the mixture was stirred at 70° C. for 6 hours. After completion of the reaction, 2M aqueous sodium hydroxide solution (45 mL) was added to the reaction mixture, and the mixture was stirred at 60° C. for 5 hours. After cooling to room temperature, the mixture was partitioned. The aqueous layer was adjusted to pH 7.0 with concentrated hydrochloric acid (4.4 mL), ethyl acetate (30 mL) and then concentrated hydrochloric acid (6.9 mL) were added, and the aqueous layer was extracted. The aqueous layer was further extracted with ethyl acetate (6 mL). The organic layers were combined, and the content of the title compound was examined by HPLC. As a result, it was found that 5.678 g of the title compound was contained in the organic solvent. The organic layer was washed 3 times with 2M hydrochloric acid (9 mL), washed with saturated brine (4.5 mL), and concentrated. Toluene (13.5 mL) was added to the concentrate, and the mixture was concentrated at 50° C. Toluene (13.5 mL) was added to the concentrate, and the mixture was stirred for 30 minutes. The mixture was cooled to 0° C. over 5 hours to allow precipitation of white crystals. The crystals were collected by filtration to give wet crystals. The powder X-ray (Cu—K$\alpha$ ray) of the wet crystals showed characteristic peaks at 17.1°, 17.6°, 18.8°, 20.7°, 21.8°, 22.0°, 22.7°, 23.1°, and 25.4°. The wet crystals were dried under reduced pressure to give the title compound as dry crystals (5.39 g). The powder X-ray (Cu—K$\alpha$ ray) of the dry crystals showed characteristic peaks at 17.1°, 21.8° 22.0°, 22.7°, 23.1°, and 25.4°. melting point 187° C.

$^1$H NMR (400 MHz, DMSO-$d_6$) $\delta$ 3.25-3.35 (m, 2H), 4.35 (d, 1H, J=7.2 Hz), 5.13 (dd, 2H, J=5.6 Hz, 10.7 Hz), 6.68-7.39 (m, 13H), 8.52 (d, 1H, J=5.6 Hz).

$^{13}$C NMR (100 MHz, DMSO-$d_6$) $\delta$ 172.49, 170.04, 162.53, 160.16, 160.12, 137.57, 137.39, 136.39, 130.45, 130.38, 130.30, 129.02, 128.29, 126.47, 115.60, 115.44, 115.39, 115.23, 55.67, 51.82, 42.18.

MS(FAB) m/z 396[M$^+$+H].

Example 1

Synthesis of L-2-acetylamino-3,3-diphenylpropanoic acid•(R)-(+)-1-(4-methylphenyl)ethylamine salt A solution (3 mL) of 2-acetylamino-3,3-diphenylpropanoic acid (1.0 g, 3.5 mmol) in methanol was heated to 60° C., and (R)-(+)-1-(4-methylphenyl)ethylamine (508 µL, 3.5 mmol) was added. The mixture was cooled to 20° C. over 4 hours with stirring and stirred for 16 hours. The precipitated crystals were collected by filtration, and dried to give the title compound (456 mg).

Example 2

Synthesis of L-2-acetylamino-3,3-diphenylpropanoic acid

To L-2-acetylamino-3,3-diphenylpropanoic acid•(R)-(+)-1-(4-methylphenyl)ethylamine salt (418 mg, 1.0 mmol) were added 2M sulfuric acid (1 mL) and ethyl acetate (3 mL), and the aqueous layer was extracted. The extract was washed with 2M sulfuric acid (1 mL) and saturated brine, concentrated and dried in vacuo to give the title compound (270 mg, optical purity 96.6% e.e. (SUMICHIRAL OA-4100, hexane:methanol:2-propanol:trifluoroacetic acid=92:4:4:0.2, 210 nm, 1.0 mL/minute, rt)).

Example 3

Synthesis of L-2-acetylamino-3,3-bis(4-fluorophenyl)propanoic acid•(R)-(+)-1-(4-methylphenyl)ethylamine salt A solution (10 mL) of 2-acetylamino-3,3-bis(4-fluorophenyl)propanoic acid (4.59 g, 14.4 mmol) in methanol was heated to 60° C. and (R)-(+)-1-(4-methylphenyl)ethylamine (2.09 mL, 14.4 mmol) was added. A seed crystal was added, and the mixture was stirred for 1 hour. The mixture was cooled to 20° C. over 4 hours with stirring and stirred for 16 hours. The precipitated crystals were collected by filtration, and dried to give the title compound (2.9 g).

Example 4

Synthesis of L-2-acetylamino-3,3-bis(4-fluorophenyl)propanoic acid

To L-2-acetylamino-3,3-bis(4-fluorophenyl)propanoic acid•(R)-(+)-1-(4-methylphenyl)ethylamine salt (2.0 g, 4.4 mmol) were added 1M hydrochloric acid (4 mL) and ethyl acetate (8 mL), and the aqueous layer was extracted. The extract was washed with 1M hydrochloric acid (2 mL) and saturated brine, concentrated, and dried in vacuo to give the title compound (1.40 g, optical purity 99.5% e.e. (SUMICHIRAL OA-4100, hexane:methanol:2-propanol:trifluoroacetic acid=92:4:4:0.2, 210 nm, 1.0 mL/minute, rt)).

Example 5

Synthesis of L-2-amino-3,3-bis(4-fluorophenyl)propanoic acid hydrochloride

A solution (10 mL) of L-2-acetylamino-3,3-bis(4-fluorophenyl)propanoic acid (1.65 g, 5.2 mmol) in concentrated hydrochloric acid was stirred for 16 hours at 90° C., and cooled with ice to allow precipitation of a solid. The solid was collected by filtration, and dried to give the title compound (1.32 g).

Example 6

Synthesis of L-2-t-butoxycarbonylamino-3,3-bis(4-fluorophenyl)propanoic acid

To an aqueous solution of L-2-amino-3,3-bis(4-fluorophenyl)propanoic acid (1.27 g, 4.05 mmol, 95.7% e.e.) was added sodium hydrogen carbonate, and its pH was adjusted to 8-9. Methanol (1.0 mL) and di-t-butyl dicarbonate (1.3 g, 5.26 mmol) were added, and the mixture was stirred at 37° C. for 16 hours. The reaction mixture was allowed to cool to room temperature, and adjusted to pH 2 with 6N hydrochloric acid. Ethyl acetate was added for partitioning, thereby to extract the object product in the organic layer. The organic layer was concentrated and heptane was added. The mixture was stirred overnight to allow precipitation of crystals. The crystals were collected by filtration and dried to give the title compound (1.24 g, optical purity 99% e.e. (SUMICHIRAL OA-4100, hexane:methanol:2-propanol:trifluoroacetic acid=98:1:1:0.1,220 nm, 1.0 mL/minute, rt)).

Example 7

Synthesis of L-2-acetylamino-3,3-bis(4-fluorophenyl)propanoic acid

To L-2-acetylamino-3,3-bis(4-fluorophenyl)propanoic acid•(R)-(+)-1-(4-methylphenyl)ethylamine salt (2.40 g, 5.3 mmol) were added 2M sulfuric acid (9.6 mL) and ethyl acetate (19.2 mL), and the aqueous layer was extracted. The extract was washed with 2M sulfuric acid (9.6 mL) and saturated brine, and concentrated. The solvent was replaced with t-butanol, water (4.8 mL) and sulfuric acid (0.8 mL) were added, and the mixture was stirred at 100° C. for 14.5 hours. Sodium hydroxide was added to adjust pH to 8-9, methanol (12 mL) and di-t-butyl dicarbonate (1.46 g, 6.34 mmol) were added, and the mixture was stirred at 35° C. for 16 hours. The reaction mixture was allowed to cool to room temperature, and adjusted to pH 2 with 6N hydrochloric acid. Ethyl acetate was added for partitioning, thereby to extract the object product in the organic layer. The organic layer was concentrated and heptane was added. The mixture was stirred overnight to allow precipitation of crystals. The crystals were collected by filtration, and dried to give the title compound (1.72 g, optical purity 99% e.e. (SUMICHIRAL OA-4100, hexane:methanol:2-propanol:trifluoroacetic acid=98:1:1:0.1, 220 nm, 1.0 mL/minute, rt)).

Example 8

Synthesis of L-2-acetylamino-3,3-diphenylpropanoic acid•(R)-(+)-1-(4-methylphenyl)ethylamine salt A solution (1 mL) of 2-acetylamino-3,3-diphenylpropanoic acid (283 mg, 1.0 mmol) in methanol was heated to 60° C., and (R)-(+)-1-(4-methylphenyl)ethylamine (145 µL, 1.0 mmol) was added. The mixture was cooled to 20° C. over 4 hours with stirring and stirred for 16 hours. The precipitated crystals were collected by filtration and dried to give the title compound (126 mg).

Example 9

Synthesis of L-2-acetylamino-3,3-diphenylpropanoic acid

To L-2-acetylamino-3,3-diphenylpropanoic acid•(R)-(+)-1-(4-methylphenyl)ethylamine salt (126 mg, 0.30 mmol) were added 1M hydrochloric acid (1 mL) and ethyl acetate (2 mL), and the aqueous layer was extracted. The extract was washed with 1M hydrochloric acid (1 mL) and saturated brine, concentrated and dried in vacuo to give the title compound (66.9 mg, optical purity 96.9% e.e. (SUMICHIRAL OA-4100, hexane:methanol:2-propanol:trifluoroacetic acid=90:5:5:0.2, 210 nm, 1.0 mL/minute, rt)).

Example 10

Synthesis of D-2-acetylamino-3,3-bis(4-fluorophenyl)propanoic acid•(S)-(−)-1-(4-methylphenyl)ethylamine salt A solution (10 mL) of 2-acetylamino-3,3-bis(4-fluorophenyl)propanoic acid (4.85 g, 15.3 mmol) in methanol was heated to 60° C., and (S)-(−)-1-(4-methylphenyl)ethylamine (2.19 mL, 15.3 mmol) was added. The mixture was cooled to 20° C. over 4 hours with stirring and stirred for 16 hours. The precipitated crystals were collected by filtration and dried to give the title compound (2.96 g).

Example 11

Synthesis of D-2-acetylamino-3,3-bis(4-fluorophenyl)propanoic acid

To D-2-acetylamino-3,3-bis(4-fluorophenyl)propanoic acid•(S)-(−)-1-(4-methylphenyl)ethylamine salt (2.96 g, 6.5 mmol) were added 2M sulfuric acid (6 mL) and ethyl acetate (24 mL), and the aqueous layer was extracted. The extract was washed with 2M sulfuric acid (6 mL) and saturated brine, concentrated and dried in vacuo to give the title compound (1.97 g, optical purity 95% e.e. (SUMICHIRAL OA-4100, hexane:methanol:2-propanol:trifluoroacetic acid=90:5:5:0.2, 210 nm, 1.0 mL/minute, rt)).

Comparative Example 1

Synthesis of D-2-acetylamino-3,3-bis(4-fluorophenyl)propanoic acid•(−)-cinchonidine salt A solution (1.0 mL) of 2-acetylamino-3,3-bis(4-fluorophenyl)propanoic acid (317 mg, 1.0 mmol) in methanol was heated to 60° C., and (−)-cinchonidine (295 mg, 1.0 mmol) was added. The mixture was cooled to 20° C. over 4 hours with stirring and stirred for 16 hours. The precipitated crystals were collected by filtration and dried to give the title compound (244 mg).

Comparative Example 2

Synthesis of D-2-acetylamino-3,3-bis(4-fluorophenyl)propanoic acid

To D-2-acetylamino-3,3-bis(4-fluorophenyl)propanoic acid•(−)-cinchonidine salt (224 g, 0.40 mmol) were added 1M hydrochloric acid (1 mL) and ethyl acetate (2 mL), and the aqueous layer was extracted. The extract was washed with 1M hydrochloric acid (1 mL) and saturated brine, concentrated, and dried in vacuo to give the title compound (129 mg, optical purity 86% e.e. (SUMICHIRAL OA-4100, hexane:methanol:2-propanol:trifluoroacetic acid=90:5:5:0.2, 210 nm, 1.0 mL/minute, rt)).

Comparative Example 3

Synthesis of D-2-acetylamino-3,3-bis(phenyl)propanoic acid (−)-cinchonidine salt A solution (1 mL) of 2-acetylamino-3,3-bis(phenyl)propanoic acid (283 mg, 1.0 mmol) in methanol was heated to 60° C., and (−)-cinchonidine (301 mg, 1.0 mmol) was added. The mixture was cooled to 20° C. over 4 hours with stirring and stirred for 16 hours. The precipitated crystals were collected by filtration and dried to give the title compound (203 mg).

Comparative Example 4

Synthesis of D-2-acetylamino-3,3-bis(phenyl)propanoic acid

To D-2-acetylamino-3,3-bis(phenyl)propanoic acid•(−)-cinchonidine salt (203 mg, 0.35 mmol) were added 1M hydrochloric acid (1 mL) and ethyl acetate (2 mL), and the aqueous layer was extracted. The extract was washed with 1M hydrochloric acid (2 mL) and saturated brine, concentrated and dried in vacuo to give the title compound (93.6 mg, optical purity 62% e.e. (SUMICHIRAL OA-4100, hexane:methanol:2-propanol:trifluoroacetic acid=90:5:5:0.2, 210 nm, 1.0 mL/minute, rt)).

INDUSTRIAL APPLICABILITY

According to the present invention, a highly pure optically active diphenylalanine compound, which is useful as a synthetic intermediate for anti-HIV drugs, dipeptidyl peptidase inhibitors and the like, can be produced conveniently in a high yield.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of producing an optically active diphenylalanine compound represented by formula (3):

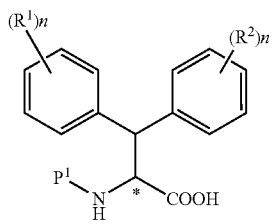

(3)

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, each n is independently an integer of 1 to 5, $P^1$ is an amino-protecting group, * indicates an asymmetric carbon atom, and the configuration of each asymmetric carbon atom is S or R, which method comprises:

(i) reacting a diphenylalanine compound represented by formula (1):

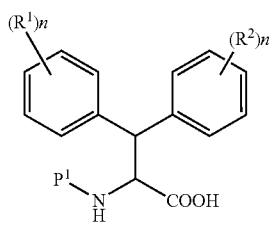

(1)

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, each n is independently an integer of 1 to 5, and $P^1$ is an amino-protecting group, with an optically active amine compound represented by formula (2):

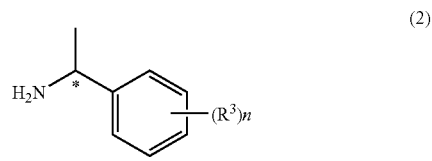

(2)

wherein $R^3$ is a hydrogen atom, a halogen atom, a substituted or unsubstituted alkyl group, a substituted or unsubstituted alkoxy group, a hydroxyl group, a protected hydroxyl group, a cyano group, a nitro group, or an acyl group, or two adjacent $R^3$ are optionally condensed to form a benzene ring, n is an integer of 1-5, * indicates an asymmetric carbon atom, and the configuration of each asymmetric carbon atom is S or R; and (ii) separating the resulting diastereomeric salt.

2. The method of claim 1, wherein said optically active amine compound comprises one or more compounds selected from the group consisting of respective optically active forms of 1-phenylethylamine, 1-(4-methylphenyl)ethylamine, 1-(4-ethylphenyl)ethylamine, 1-(4-propylphenyl)ethylamine, 1-(4-isopropylphenyl)ethylamine, 1-(4-methoxyphenyl)ethylamine, 1-(4-bromophenyl)ethylamine, 1-(4-chlorophenyl)ethylamine, 1-(4-fluorophenyl)ethylamine, 1-(4-hydroxyphenyl)ethylamine, 1-(4-cyanophenyl)ethylamine, 1-(4-nitrophenyl)ethylamine, 1-(4-acetylphenyl)ethylamine, 1-(1-naphthyl)ethylamine, 1-(2-naphthyl)ethylamine, and mixtures thereof.

3. The method of claim 1, wherein said optically active amine compound comprises one or more compounds selected from the group consisting of (−)-1-phenylethylamine, (+)-1-phenylethylamine, (−)-1-(4-methylphenyl)ethylamine, (+)-1-(4-methylphenyl)ethylamine, (−)-1-(4-isopropylphenyl)ethylamine, (+)-1-(4-isopropylphenyl)ethylamine, (−)-1-(4-methoxyphenyl)ethylamine, (+)-1-(4-methoxyphenyl)ethylamine, (−)-1-(4-bromophenyl)ethylamine, (+)-1-(4-bromophenyl)ethylamine, (−)-1-(4-chlorophenyl)ethylamine, (+)-1-(4-chlorophenyl)ethylamine, (−)-1-(1-naphthyl)ethylamine, (+)-1-(1-naphthyl)ethylamine, (−)-1-(2-naphthyl)ethylamine, (+)-1-(2-naphthyl)ethylamine, and mixtures thereof.

4. The method of claim 1, wherein said optically active amine compound comprises one or more compounds selected from the group consisting of (−)-1-phenylethylamine, (+)-1-phenylethylamine, (−)-1-(4-methylphenyl)ethylamine, (+)-1-(4-methylphenyl)ethylamine, and mixtures thereof.

5. The method of claim 1, wherein said separating comprises crystal precipitation of the diastereomeric salt in one or more kinds of solvents selected from the group consisting of water, methanol, ethanol, 2-propanol, ethyl acetate, benzene, toluene, xylene, cyclohexane, methylcyclohexane, 1,2-dichloroethane, tert-butyl methyl ether, isobutyl methyl ketone, butyl acetate, chlorobenzene, tetrahydrofuran, N,N-dimethylformamide, N,N-dimethylacetamide, dimethyl sulfoxide, N-methyl-2-pyrrolidone, acetonitrile, and mixtures thereof.

6. A method of producing an optically active diphenylalanine compound represented by formula (4):

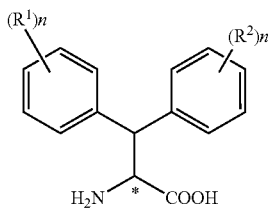

(4)

wherein $R^1$ and $R^2$ are each independently a hydrogen atom, a halogen atom, a substituted or unsubstituted alkyl group, a substituted or unsubstituted alkoxy group, a substituted or unsubstituted amino group, a nitro group, a hydroxyl group, or a protected hydroxyl group, each n is independently an integer of 1 to 5, * indicates an asymmetric carbon atom, and the configuration of each asymmetric carbon atom is S or R, which method comprises:
(i) obtaining an optically active diphenylalanine compound represented by formula (3) according to the method of claim 1; and
(ii) removing the amino-protecting group from said compound represented by formula (3).

7. The method of claim 1, wherein $R^1$ and $R^2$ are each independently a fluorine atom or a hydrogen atom, and $P^1$ is an acetyl group.

8. The method of claim 6, wherein $R^1$ and $R^2$ are each independently a fluorine atom or a hydrogen atom, and $P^1$ is an acetyl group.

9. The method of claim 2, wherein $R^1$ and $R^2$ are each independently a fluorine atom or a hydrogen atom, and $P^1$ is an acetyl group.

10. The method of claim 3, wherein $R^1$ and $R^2$ are each independently a fluorine atom or a hydrogen atom, and $P^1$ is an acetyl group.

11. The method of claim 4, wherein $R^1$ and $R^2$ are each independently a fluorine atom or a hydrogen atom, and $P^1$ is an acetyl group.

12. The method of claim 5, wherein $R^1$ and $R^2$ are each independently a fluorine atom or a hydrogen atom, and $P^1$ is an acetyl group.

13. The method of claim 6, wherein said optically active amine compound comprises one or more compounds selected from the group consisting of respective optically active forms of 1-phenylethylamine, 1-(4-methylphenyl)ethylamine, 1-(4-ethylphenyl)ethylamine, 1-(4-propylphenyl)ethylamine, 1-(4-isopropylphenyl)ethylamine, 1-(4-methoxyphenyl)ethylamine, 1-(4-bromophenyl)ethylamine, 1-(4-chlorophenyl)ethylamine, 1-(4-fluorophenyl)ethylamine, 1-(4-hydroxyphenyl)ethylamine, 1-(4-cyanophenyl)ethylamine, 1-(4-nitrophenyl)ethylamine, 1-(4-acetylphenyl)ethylamine, 1-(1-naphthyl)ethylamine, 1-(2-naphthyl)ethylamine, and mixtures thereof.

14. The method of claim 6, wherein said optically active amine compound comprises one or more compounds selected from the group consisting of (−)-1-phenylethylamine, (+)-1-phenylethylamine, (−)-1-(4-methylphenyl)ethylamine, (+)-1-(4-methylphenyl)ethylamine, (−)-1-(4-isopropylphenyl)ethylamine, (+)-1-(4-isopropylphenyl)ethylamine, (−)-1-(4-methoxyphenyl)ethylamine, (+)-1-(4-methoxyphenyl)ethylamine, (−)-1-(4-bromophenyl)ethylamine, (+)-1-(4-bromophenyl)ethylamine, (−)-1-(4-chlorophenyl)ethylamine, (+)-1-(4-chlorophenyl)ethylamine, (−)-1-(1-naphthyl)ethylamine, (+)-1-(1-naphthyl)ethylamine, (−)-1-(2-naphthyl)ethylamine, (+)-1-(2-naphthyl)ethylamine, and mixtures thereof.

15. The method of claim 6, wherein said optically active amine compound comprises one or more compounds selected from the group consisting of (−)-1-phenylethylamine, (+)-1-phenylethylamine, (−)-1-(4-methylphenyl)ethylamine, (+)-1-(4-methylphenyl)ethylamine, and mixtures thereof.

16. The method of claim 6, wherein said separating comprises crystal precipitation of the diastereomeric salt in one or more kinds of solvents selected from the group consisting of water, methanol, ethanol, 2-propanol, ethyl acetate, benzene, toluene, xylene, cyclohexane, methylcyclohexane, 1,2-dichloroethane, tert-butyl methyl ether, isobutyl methyl ketone, butyl acetate, chlorobenzene, tetrahydrofuran, N,N-dimethylformamide, N,N-dimethylacetamide, dimethyl sulfoxide, N-methyl-2-pyrrolidone, acetonitrile, and mixtures thereof.

17. The method of claim 1, further comprising:
(iii) converting said diastereomeric salt to said optically active diphenylalanine compound represented by formula (3).

18. The method of claim 2, further comprising:
(iii) converting said diastereomeric salt to said optically active diphenylalanine compound represented by formula (3).

19. The method of claim 3, further comprising:
(iii) converting said diastereomeric salt to said optically active diphenylalanine compound represented by formula (3).

20. The method of claim 4, further comprising:
(iii) converting said diastereomeric salt to said optically active diphenylalanine compound represented by formula (3).

21. The method of claim 5, further comprising:
(iii) converting said diastereomeric salt to said optically active diphenylalanine compound represented by formula (3).

22. The method of claim 17, wherein said optically active diphenylalanine compound represented by formula (3) has an e.e. of not less than 95%.

23. The method of claim 18, wherein said optically active diphenylalanine compound represented by formula (3) has an e.e. of not less than 95%.

24. The method of claim 19, wherein said optically active diphenylalanine compound represented by formula (3) has an e.e. of not less than 95%.

25. The method of claim 20, wherein said optically active diphenylalanine compound represented by formula (3) has an e.e. of not less than 95%.

26. The method of claim 21, wherein said optically active diphenylalanine compound represented by formula (3) has an e.e. of not less than 95%.

* * * * *

UNITED STATES PATENT AND TRADEMARK OFFICE
CERTIFICATE OF CORRECTION

| | | |
|---|---|---|
| PATENT NO. | : 7,321,055 B2 | Page 1 of 1 |
| APPLICATION NO. | : 11/498752 | |
| DATED | : January 22, 2008 | |
| INVENTOR(S) | : Hamada et al. | |

It is certified that error appears in the above-identified patent and that said Letters Patent is hereby corrected as shown below:

On the title page, Item (54), and Column 1, the title information is incorrect. Item (54) and Column 1 should read:

-- (54)   PRODUCTION METHOD OF OPTICALLY ACTIVE DIPHENYLALANINE COMPOUNDS --

Signed and Sealed this

Nineteenth Day of August, 2008

JON W. DUDAS
*Director of the United States Patent and Trademark Office*